US009409853B2

(12) United States Patent
Schuch et al.

(10) Patent No.: US 9,409,853 B2
(45) Date of Patent: Aug. 9, 2016

(54) POLYGLYCEROL PARTIAL ESTERS, PREPARATION AND USE THEREOF

(71) Applicants: Dominik Schuch, Haan (DE); Wolfgang Berkels, Bottrop (DE); Oliver Springer, Wesel (DE); Christian Hartung, Essen (DE); Hilke Condé, Gladbeck (DE); Baerbel Klann-Metz, Essen (DE)

(72) Inventors: Dominik Schuch, Haan (DE); Wolfgang Berkels, Bottrop (DE); Oliver Springer, Wesel (DE); Christian Hartung, Essen (DE); Hilke Condé, Gladbeck (DE); Baerbel Klann-Metz, Essen (DE)

(73) Assignee: EVONIK DEGUSSA GMBH, Essen (DE)

( * ) Notice: Subject to any disclaimer, the term of this patent is extended or adjusted under 35 U.S.C. 154(b) by 4 days.

(21) Appl. No.: 14/564,408

(22) Filed: Dec. 9, 2014

(65) Prior Publication Data

US 2015/0315123 A1    Nov. 5, 2015

(30) Foreign Application Priority Data

Dec. 5, 2013 (DE) .................. 10 2013 224 957

(51) Int. Cl.
| | | |
|---|---|---|
| *C07C 59/00* | (2006.01) | |
| *C07C 69/52* | (2006.01) | |
| *C07C 67/08* | (2006.01) | |
| *A61K 8/37* | (2006.01) | |
| *C07C 69/732* | (2006.01) | |
| *A61K 8/39* | (2006.01) | |
| *A61Q 1/14* | (2006.01) | |
| *A61Q 5/02* | (2006.01) | |
| *A61Q 15/00* | (2006.01) | |
| *A61K 8/86* | (2006.01) | |
| *A61Q 19/10* | (2006.01) | |

(52) U.S. Cl.
CPC ................ *C07C 69/52* (2013.01); *A61K 8/375* (2013.01); *A61K 8/39* (2013.01); *A61K 8/86* (2013.01); *A61Q 1/14* (2013.01); *A61Q 5/02* (2013.01); *A61Q 15/00* (2013.01); *A61Q 19/10* (2013.01); *C07C 67/08* (2013.01); *C07C 69/732* (2013.01); *A61K 2800/30* (2013.01); *A61K 2800/49* (2013.01)

(58) Field of Classification Search
CPC ...... C07C 69/52; C07C 67/08; C07C 69/732; A61K 8/375; A61K 8/39; A61K 8/86; A61O 1/14; A01O 5/02; A01O 15/00; A01O 19/10
USPC .......................................... 554/219
See application file for complete search history.

(56) References Cited

U.S. PATENT DOCUMENTS

| | | |
|---|---|---|
| 5,840,943 A | 11/1998 | Ansmann et al. |
| 6,581,613 B2 | 6/2003 | Berkels et al. |
| 7,851,511 B2 | 12/2010 | Allef et al. |
| 7,906,664 B2 | 3/2011 | Allef et al. |
| 8,211,972 B2 | 7/2012 | Meyer et al. |
| 8,642,525 B2 | 2/2014 | Herrwerth et al. |
| 2013/0071340 A1 | 3/2013 | Wenk et al. |
| 2013/0171087 A1 | 7/2013 | Herrwerth et al. |
| 2013/0204021 A1 | 8/2013 | Hartung et al. |
| 2013/0281552 A1 | 10/2013 | Nilewski et al. |
| 2014/0072521 A1 | 3/2014 | Meyer et al. |

FOREIGN PATENT DOCUMENTS

| | | |
|---|---|---|
| EP | 1197559 | 4/2002 |
| EP | 2273966 | 1/2011 |
| JP | 2008119568 | 5/2008 |
| WO | WO2004041769 | 5/2004 |
| WO | WO2007027447 A1 | 3/2007 |
| WO | WO2009138306 A1 | 11/2009 |

OTHER PUBLICATIONS

Wilson, R., et al., "Overview of the Preparation, Use and Biological Studies on Polygycerol Polyricinoleate (PGPR)", Food and Chemical Toxicology, Jan. 1998, p. 721, 36.
European Search Report dated Apr. 23, 2015, received in a corresponding foreign application.
Schrader, K. et al., "Grundlagen and Rezepturen der Kosmetika" ["Principles and Formulations of Cosmetics"], 1989, 2nd edition, p. 329 to 341, Hüthig Buch Verlag Heidelberg.
Cassel, S., et al., "Original Synthesis of Linear, Branched and Cyclic Oligoglycerol Standards", European Journal of Organic Chemistry, Mar. 2001, vol. 2001, Issue 5, pp. 875-896.

*Primary Examiner* — Deborah D Carr
(74) *Attorney, Agent, or Firm* — Scully, Scott, Murphy & Presser, P.C.

(57) ABSTRACT

Polyglycerol partial esters of a specific composition which are capable of solubilizing very hydrophobic, oil-soluble substances in aqueous solution are provided. The preparation and use of these polyglycol ether-free solubilizers in cosmetic formulations are also disclosed.

18 Claims, No Drawings

POLYGLYCEROL PARTIAL ESTERS, PREPARATION AND USE THEREOF

FIELD OF THE INVENTION

The present invention relates to polyglycerol partial esters of a specific composition which are capable of solubilizing very hydrophobic, oil-soluble substances in aqueous solution. The present invention also relates to the preparation and use of these polyglycol ether-free solubilizers in cosmetic formulations.

PRIOR ART

Non-ionic surfactants having hardly any foam-generating effect are usually employed as solubilizers of oil-soluble, hydrophobic substances in water.

Polyethoxylated triglycerides, particularly based on castor oil, e.g., PEG-40 hydrogenated castor oil, are used as standard solubilizers. The latter is virtually able to clearly solubilize oil-soluble substances of a wide variety of structures and hydrophobicity in water. Polyglycol ether-free polyglycerol partial esters have also been used for some years as alternative solubilizers.

The disadvantage of all polyglycerol partial esters available to date is that their use as solubilizers of oil-soluble substances in water cannot cover as wide a substance spectrum as the previously mentioned polyethoxylated triglycerides. The polyglycerol esters are thus mainly suitable for solubilizing "small" molecules such as, for example, short-chain terpenes. In contrast, oils based on fatty acids and triglycerides of long-chain fatty acids such as jojoba oil, almond oil, soybean oil or avocado oil cannot, to date, be clearly solubilized in water using the commercial products based on polyglycerol partial esters.

JP 2008-119568 describes the use of polyglycerol partial esters as solubilizers of oils in which the polyglycerol partial esters are based on mixtures of saturated fatty acids having 8 to 22 carbon atoms and unsaturated fatty acids having 16 to 22 carbon atoms, wherein the molar ratio of saturated to unsaturated fatty acids is in a range of 0.2 to 0.8 to 0.8 to 0.2. In addition, polyglycerol partial esters of polyricinoleic acid may be admixed with this polyglycerol partial ester.

SUMMARY OF THE INVENTION

One object of the present invention is to provide solubilizers based on polyglycerol partial esters which, in contrast to the products available on the market to date, are able to clearly solubilize, in particular, hydrophobic, oil-soluble substances, such as long-chain triglycerides, in water and to solubilize cosmetic formulations.

It has been surprisingly found that the polyglycerol partial esters described in the present invention are able to rectify the disadvantages of the prior art and thus enable to achieve the object of the present invention mentioned above.

In one embodiment of the present invention, polyglycerol partial esters are provided which are prepared from polyglycerol by esterification of a specifically selected fatty acid mixture. The products are able to clearly solubilize very hydrophobic, oil-soluble substances, such as long-chain triglycerides, in water or to solubilize a cosmetic formulation. The preparation and use of these solubilizers in cosmetic formulations is also part of this invention.

An advantage of the present invention is that the polyglycerol partial esters described herein are able to clearly solubilize strongly hydrophobic, oil-soluble substances, such as long-chain triglycerides, in water or to solubilize a cosmetic formulation, which is not possible using the products based on polyglycerol esters available to date.

A further advantage of the present invention is that the polyglycerol partial esters described herein may be prepared exclusively from renewable raw materials in contrast to polyethoxylated triglycerides.

A yet further advantage of the present invention is that the polyglycerol partial esters described herein are liquid, and thus readily processable, in contrast to polyethoxylated triglycerides.

An even further advantage of the present invention compared to the polyethoxylated triglycerides is that the polyglyceryl esters described herein lead to particularly clear dispersions of the oil in the water, and also no cloudiness occurs on storage, in contrast to polyethoxylated triglycerides (PEG-40 hydrogenated castor oil).

Another advantage of the present invention is that formulations may be provided that are polyglycol ether-free.

A further advantage of the polyglycerol partial esters described herein is that the polyglycerol partial esters of the present invention can produce a pleasant skin sensation in cosmetic formulations.

Another advantage of the polyglycerol partial esters described herein is that the polyglycerol partial esters of the present invention exhibit only a very low foam formation on stirring in water.

A further advantage is that the polyglycerol partial esters described herein show only a very low effect on foamability and foam quantity in surfactant formulations, but the foam creaminess can, however, improve.

Another advantage is that the polyglycerol partial esters described in the present invention may lead to attenuation of the skin irritancy in surfactant formulations.

A further advantage of the polyglycerol partial esters described herein is that the polyglycerol partial esters of the present invention can have a stabilizing effect in emulsions.

A further advantage of the inventive products is that they are relatively stable to oxidation and more stable with respect to color, odor and appearance.

DETAILED DESCRIPTION OF THE INVENTION

The present invention provides polyglycerol partial esters of general formula I

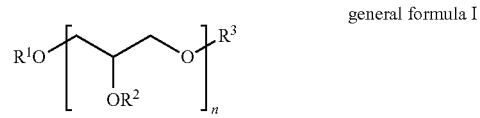

general formula I where
n=2 to 16, preferably 4 to 14, particularly preferably 5 to 11,
$R^1$, $R^2$, $R^3$=independently of one another, identical or different, selected from H, $R^4$ and
$R^5$, where
$R^4$=saturated or unsaturated acyl residue having 6-22 carbon atoms, preferably 8-18 carbon atoms, comprising no hydroxyl groups,
$R^5$=saturated or unsaturated acyl residue having 6-22 carbon atoms, preferably 14-22 carbon atoms, comprising at least one hydroxyl group or an acyl residue of an oligomer of saturated or unsaturated acyl residues having 6-22 carbon atoms, preferably 14-22 carbon atoms, comprising at least one hydroxyl group, in which the acyl residue of the oligomer preferably has 26 to 66 carbon atoms,
characterized in that the molar ratio of the acyl residues $R^4$ to $R^5$ is in a range of 95:5 to 5:95, preferably 85:15 to 15:85, particularly preferably 85:15 to 50:50.

A person skilled in the art is aware that the polyglycerol base skeleton present in general formula I, owing to its polymeric property, represents a random mixture of various compounds. Polyglycerol may have formed ether bonds between two primary, one primary and one secondary and also two secondary positions of the glycerol monomers. For this reason, the polyglycerol base skeleton does not usually consist exclusively of linearly linked glycerol units, but may also comprise branches and rings. For details see, e.g., "*Original synthesis of linear, branched and cyclic oligoglycerol standards*", Cassel et al., *J Org. Chem.* 2001, 875-896.

Structures of this kind are covered in this respect in the simplified, general formula I.

From the term "the molar ratio of the acyl residues $R^4$ to $R^5$ is in a range of 95:5 to 5:95", it is clear that residues $R^4$ and $R^5$ are present in the polyglycerol partial esters according to the invention.

Preferred polyglycerol partial esters according to the invention are characterized in that they comprise structures of general formula 1) each having at the same time at least one $R^4$ residue and one $R^5$ residue.

The acyl residues $R^4$ and $R^5$ can be randomly attached to the polyglycerol base skeleton both via primary and via secondary hydroxyl groups.

All conditions such as, for example, pressure and temperature, if not stated otherwise, are standard conditions (20° C., 1 bar). Percentages are indicated, if not described otherwise, in mass percent.

The degree of polymerisation 'n' can thus be determined, whereby the hydroxyl number of the polyglycerol used for the synthesis of the inventive ester is determined, in which the mean degree of polymerisation n is related to the hydroxyl number of the polyglycerol on which it is based via the following equation:

$$n = \frac{\frac{2000 \cdot M(\text{KOH})}{\text{OHZ}} - M(\text{Water})}{\left[ [M(\text{Glycerol}) - M(\text{Water})] - \frac{1000 \cdot M(\text{KOH})}{\text{OHZ}} \right]}$$

where M=molar mass; OHZ=hydroxyl number of the free polyglycerol.

Alternatively, the degree of polymerisation 'n' can also be determined by determining the hydroxyl number of the polyglycerol obtained after complete ester hydrolysis.

Suitable methods for determining the hydroxyl number are particularly those according to DGF C-V 17 a (53), Ph. Eur. 2.5.3 Method A and DIN 53240.

The acyl residues $R^4$ and $R^5$ are preferably acyl residues of fatty acids. $R^4$ and $R^5$ may also represent mixtures of such acyl residues, particularly technical mixtures such as, in the case of $R^4$, coconut fatty acid cuts.

For $R^4$, it is with particular preference that at least 50 mol %, preferably at least 75 mol %, of the $R^4$ acyl residues are selected from capryloyl, caproyl and lauroyl residues, based on all $R^4$ residues in the polyglycerol partial ester.

$R^5$ is particularly preferably selected from ricinoyl and hydroxystearoyl residues, their oligomers and mixtures thereof, particularly preferably at least 90 mol % of the $R^5$ acyl residues comprise ricinoyl residues or a mixture of ricinoyl and hydroxystearoyl residues, based on all $R^5$ residues in the polyglycerol partial ester, in which it is preferred that the mixture of ricinoyl and hydroxystearoyl residues has a molar ratio of ricinoyl to hydroxystearoyl residues in a range of 100 to 0.1 to 50 to 50.

As an alternative, $R^5$ is preferably selected from ricinoyl residues.

Preferred polyglycerol partial esters according to the invention are characterized in that the weight ratio of the polyglyceryl residue to the sum total of the acyl residues $R^4$ and $R^5$ is 85:15 to 55:45, preferably 80:20 to 60:40, particularly preferably 75:25 to 65:35.

Preferred polyglycerol partial esters according to the invention are further characterized in that the molar ratio of saturated to unsaturated acyl residues in the sum total of all $R^4$ and $R^5$ residues is 99:1-1:99, preferably 95:5-50:50, particularly preferably 90:10-60:40.

The polyglycerol partial esters of the present invention can be prepared by classical esterification and transesterification methods, preferably by the inventive method described hereinafter.

The present invention further relates to a method for preparing polyglycerol partial esters comprising the method steps of:
  A) providing a polyglycerol having a mean degree of polymerisation n=2 to 16, preferably 4-14, particularly preferably 5-11,
  B) acylation of some of the hydroxyl groups of the polyglycerol with
at least one first carboxylic acid derivative of one or more first, saturated or unsaturated carboxylic acids having 6-22 carbon atoms, preferably 8-18 carbon atoms, comprising no hydroxyl groups and
at least one second carboxylic acid derivative of one or more second, saturated or unsaturated carboxylic acids having 6-22 carbon atoms, preferably 14-22 carbon atoms, comprising at least one hydroxyl group or an oligomer of the second carboxylic acid, wherein the oligomer preferably has 26 to 66 carbon atoms,
in which the carboxylic acid derivatives are selected from carboxylic acids and carboxylic esters, wherein triglycerides are preferred as carboxylic esters in accordance with the invention,
wherein the molar ratio of the acyl residues of the first carboxylic acid derivative used in method step B) to those of the second carboxylic acid derivative is in a range of 95:5 to 5:95, preferably 85:5 to 15:85, particularly preferably 85:15 to 50:50.

The carboxylic acid derivatives preferably used in the method according to the invention are fatty acid derivatives.

In the method according to the invention, therefore, in method step B)
at least one first carboxylic acid and at least one second carboxylic acid,
at least one first carboxylic ester and at least one second carboxylic acid,
at least one first carboxylic acid and at least one second carboxylic ester,
at least one first carboxylic ester and at least one second carboxylic ester,
at least one first carboxylic acid and at least one first carboxylic ester and at least one second carboxylic acid,
at least one first carboxylic acid and at least one first carboxylic ester and at least one second carboxylic ester,
at least one first carboxylic acid and at least one second carboxylic acid and at least one second carboxylic ester, at least one first carboxylic ester and at least one second carboxylic acid and at least one second carboxylic ester,
or
at least one first carboxylic acid and at least one first carboxylic ester and at least one second carboxylic acid and at least one second carboxylic ester,
may be used.

A preferred method according to the invention is characterized in that at least 50 mol %, preferably at least 75 mol %, of the first carboxylic acids are selected from caprylic acid, capric acid and lauric acid, based on the acyl residues of all the first carboxylic acid derivatives.

It is preferred in accordance with the invention, in the method according to the invention, that at least 90 mol % of the second carboxylic acids are selected from ricinoleic acid and hydroxystearic acid, based on the acyl residues of all the second carboxylic acid derivatives.

A preferred method according to the invention is characterized in that at least 90 mol % of the second carboxylic acids comprise ricinoleic acid and/or hydroxystearic acid, wherein the second carboxylic acids preferably have a molar ratio of ricinoleic acid residues to hydroxystearic acid residues in a range of 100 to 0.1 to 50 to 50, based on the acyl residues of all the second carboxylic acid derivatives.

Alternatively, the second carboxylic acid derivative is preferably selected from ricinoleic acid or castor oil.

It is preferred, in the method according to the invention, that the weight ratio of the polyglycerol to the calculated sum total of the acyl residues of the first and second carboxylic acid derivatives used is 85:15 to 55:45, preferably 80:20 to 60:40, particularly preferably 75:25 to 65:35.

A preferred method according to the invention is characterized in that the molar ratio of the acyl residues of saturated to those of the unsaturated carboxylic acid derivatives used in method step B) is 99:1-1:99, preferably 95:5-50:50, particularly preferably 90:10-60:40.

The present invention furthermore relates to polyglycerol partial esters, obtainable by the method according to the invention, wherein the preferred partial esters according to the invention are those which are obtainable by the preferred method according to the invention.

The present invention further relates to formulations, particularly cosmetic and pharmaceutical formulations, wherein particular preference is given to cosmetic formulations which comprise at least one polyglycerol partial ester according to the invention and/or at least one polyglycerol partial ester obtainable by the method according to the invention.

Particular preference is given to formulations which are essentially polyglycol ether-free and essentially free of alkoxylated compounds. The term "essentially free of alkoxylated compounds" and "essentially polyglycol ether-free", in connection with the present invention, are understood to mean that the formulations have no notable amounts of alkoxylated compounds or compounds comprising polyglycol ethers which exert a surface-active effect. This is particularly understood to mean that these compounds are present in amounts of less than 1% by weight, preferably less than 0.1% by weight, particularly preferably less than 0.01% by weight, based on the total formulation, in particular no detectable amounts.

The polyglycerol partial esters of the present invention can be used advantageously for preparing care and cleaning formulations, particularly for skin and skin appendages, such as liquid soaps, shower gels, oil baths, make-up removers or shampoos, shower gels, foam baths, liquid soaps, hair shampoos, 2-in-1 shampoos, hair conditioners, permanent wave fixing solutions, hair colouring shampoos, hair setting compositions, hair treatments, hair arranging compositions, hair styling compositions, blow-drying lotions, setting foams, hair treatments, leave-in conditioners, hair smoothing compositions, shine improving compositions and compositions for colouring the hair. The present invention therefore also relates to such uses.

The present invention thus also provides care and cleaning formulations, in particular for skin and skin appendages, comprising polyglycerol partial esters according to the invention.

The term "care formulation" is herein understood to mean a formulation which satisfies the purpose of restoring an object to its original form, of reducing or avoiding the effects of external influences (e.g., time, light, temperature, pressure, soiling, chemical reaction with other reactive compounds that come into contact with the object) such as ageing, soiling, material fatigue, bleaching or even of improving desired positive properties of the object. For the last point, mention may be made for example of a shine of the object under consideration.

Cosmetic care and cleaning formulations according to the invention can, for example, comprise at least one additional component selected from the group of:
emollients,
emulsifiers,
thickeners/viscosity regulators/stabilizers,
antioxidants,
hydrotropes (or polyols),
solids and fillers,
pearlescence additives,
deodorant and antiperspirant active ingredients,
insect repellents,
self-tanning agents,
preservatives,
conditioners,
perfumes,
dyes,
cosmetic active ingredients,
care additives,
superfatting agents,
solvents.

Substances which can be used as exemplary representatives of the individual groups are known to a person skilled in the art and can be found, for example, in EP2273966A1. This patent application is herewith incorporated as reference and thus forms part of the disclosure.

As regards to further optional components and the amounts of these components used, reference is made expressly to the relevant handbooks known to a person skilled in the art, e.g., K. Schrader, "Grundlagen and Rezepturen der Kosmetika [Fundamentals and Formulations of Cosmetics]", 2nd edition, pages 329 to 341, Hüthig Buch Verlag Heidelberg.

The amounts of the particular additives are governed by the intended use. Typical guide formulations for the respective applications are known prior art and are contained for example in the brochures of the manufacturers of the particular basic materials and active ingredients. These existing formulations can usually be adopted unchanged. If necessary, the desired modifications can, however, be undertaken without complication by means of simple experiments for the purposes of adaptation and optimization.

Preferred formulation according to the invention comprise preferred polyglycerol partial esters according to the invention as set out above or preferred polyglycerol partial esters according to the invention obtainable by the method according to the invention as set out above.

It is preferred if the formulation according to the invention additionally comprise at least one oil-soluble substance and water.

In the present invention, oil-soluble substances are understood to mean substances having a log P (logarithm of n-octanol/water partition coefficient, also known as log $K_{OW}$) of at least 2.

Preference is given to oil-soluble substances having a log P of at least 5. Particular preference is given to oil-soluble substances selected from the group comprising oils based on fatty acids, triglycerides of long-chain fatty acids, cosmetic ester oils, pure hydrocarbons such as jojoba oil, almond oil, soybean oil, avocado oil, olive oil, argan oil, rapeseed oil, sunflower oil, neem oil, caprylic/capric acid triglyceride, shea butter, decyl cocoate, isopropyl palmitate, myristyl myristate and isohexadecane.

Particularly preferred formulations according to the invention comprise 0.1% by weight to 40% by weight, preferably 0.3% by weight to 35% by weight, particularly preferably 0.5% by weight to 10% by weight, of polyglycerol partial ester according to the invention and/or polyglycerol partial ester obtainable by the method according to the invention, 0.01% by weight to 40% by weight, preferably 0.1% by weight to 30% by weight, particularly preferably 0.2% by weight to 2% by weight, of oil-soluble substance and 10% by weight to 98% by weight, preferably 20% by weight to 95% by weight, particularly preferably 45% by weight to 90% by weight, of water.

The present invention also relates to the use of at least one polyglycerol partial ester according to the invention and/or at least one polyglycerol partial ester obtainable by the method according to the invention for solubilizing at least one oil-soluble substance in water, wherein it is preferable in accordance with the invention that preferred polyglycerol partial esters according to the invention as set out above or preferred polyglycerol partial esters according to the invention obtainable by the method according to the invention as set out above are used.

The examples listed below describe the present invention by way of example, without any intention of restricting the invention, the scope of application of which is apparent from the entirety of the description and the claims, to the embodiments specified in the examples.

EXAMPLES

Example 1

Preparing Inventive Polyglycerol Partial Esters 1.1 Preparation of Polyglycerol Partial Ester A:

Under a nitrogen atmosphere, 225 g of polyglycerol (hydroxyl number=935 mg KOH/g) were stirred with 39.4 g of caprylic/capric acid and 20.8 g of refined coconut fatty acid and 22.1 g of ricinoleic acid and 15.5 g of hydroxystearic acid at 240° C. until an acid number<0.5 mg KOH/g was achieved. The water formed during the course of the reaction was continuously distilled off. After cooling to room temperature, the reaction product was in the form of a turbid liquid.

1.2 Preparation of Polyglycerol Partial Ester B:

Under a nitrogen atmosphere, 225 g of polyglycerol (hydroxyl number=996 mg KOH/g) were stirred with 39.4 g of caprylic/capric acid and 20.8 g of refined coconut fatty acid and 22.1 g of ricinoleic acid and 15.5 g of hydroxystearic acid at 240° C. until an acid number<0.5 mg KOH/g was achieved. The water formed during the course of the reaction was continuously distilled off. After cooling to room temperature, the reaction product was in the form of a turbid liquid.

1.3. Preparation of Polyglycerol Partial Ester C:

Under a nitrogen atmosphere, 225 g of polyglycerol (hydroxyl number=935 mg KOH/g) were stirred with 47.3 g of caprylic/capric acid and 20.8 g of refined coconut fatty acid and 17.7 g of ricinoleic acid and 12.4 g of hydroxystearic acid at 240° C. until an acid number<0.5 mg KOH/g was achieved. The water formed during the course of the reaction was continuously distilled off. After cooling to room temperature, the reaction product was in the form of a turbid liquid.

1.4. Preparation of Polyglycerol Partial Ester D:

Under a nitrogen atmosphere, 202 g of polyglycerol (hydroxyl number=884 mg KOH/g) were stirred with 37.7 g of caprylic/capric acid and 24.9 g of refined coconut fatty acid and 23.5 g of ricinoleic acid and 12.4 g of hydroxystearic acid at 240° C. until an acid number<0.5 mg KOH/g was achieved. The water formed during the course of the reaction was continuously distilled off. After cooling to room temperature, the reaction product was in the form of a turbid liquid.

1.5. Preparation of Polyglycerol Partial Ester E:

Under a nitrogen atmosphere, 225 g of polyglycerol (hydroxyl number=935 mg KOH/g) were stirred with 39.4 g of caprylic/capric acid and 23.0 g of refined coconut oil and 41.5 g of castor oil at 240° C. until an acid number<0.5 mg KOH/g was achieved. The water formed during the course of the reaction was continuously distilled off. After cooling to room temperature, the reaction product was in the form of a turbid liquid.

1.6. Preparation of Polyglycerol Partial Ester F:

Under a nitrogen atmosphere, 225 g of polyglycerol (hydroxyl number=935 mg KOH/g) were stirred with 39.4 g of caprylic/capric acid and 23.0 g of refined coconut oil and 23.0 g of castor oil and 14.2 g of castor wax at 240° C. until an acid number<0.5 mg KOH/g was achieved. The water formed during the course of the reaction was continuously distilled off. After cooling to room temperature, the reaction product was in the form of a turbid liquid.

1.7. Preparation of Polyglycerol Partial Ester G:

In a first reaction, 225 g of polyglycerol (hydroxyl number=935 mg KOH/g) were stirred under a nitrogen atmosphere with 38.0 g of caprylic acid and 60 g of castor oil at 240° C. until an acid number<0.5 mg KOH/g was achieved. The water formed during the course of the reaction was continuously distilled off.

In a second reaction, 225 g of polyglycerol (hydroxyl number=1060 mg KOH/g) were reacted under identical reaction conditions with 41.0 g of capric acid, 23 g of castor oil and 46.0 g of refined coconut oil.

The two products were then combined and stirred at 90° C. until a clear, homogeneous mixture was formed, which, after cooling to room temperature, was in the form of a turbid liquid.

Example 2

Preparing Non-Inventive Polyglycerol Partial Esters 2.1. Preparation of Polyglycerol Partial Ester H:

Under a nitrogen atmosphere, 394 g of polyglycerol (hydroxyl number=1061 mg KOH/g) were stirred with 51.3 g of caprylic/capric acid and 23.0 g of refined coconut fatty acid and 32.8 g of oleic acid at 240° C. until an acid number<0.5 mg KOH/g was achieved. The water formed during the course of the reaction was continuously distilled off. After cooling to room temperature, the reaction product was in the form of a turbid liquid.

Example 3

Non-Inventive, Commercial Comparative Examples 3.1. TEGOSOFT® PC 41:
Standard solubilizer, polyether-free. INCI: Polyglyceryl-4 caprate. Commercial product of Evonik Industries AG.
3.2. NATRAGEM® S 150 NP-LQ-(CM):
Solubilizer for oils, polyether-free. INCI: Polyglyceryl-4 laurate/sebacate (and) polyglyceryl-4 caprylate/caprate (and) water. Commercial product of Croda.
3.3. TAGAT® CH 40:
Standard solubilizer, polyether-containing. INCI: PEG-40 Hydrogenated castor oil. Commercial product of Evonik Industries AG.

The products described above were tested in cosmetic formulations below.

The formulation constituents are named in the compositions in the form of the generally recognized INCI nomenclature using the English terms. All concentrations are given in the application examples in percent by weight.

Example 4

Improved Dissolving Power of the Inventive Polyglycerol Partial Esters in Aqueous Solutions in Comparison to the Non-Inventive Polyglycerol Partial Esters In order to investigate the dissolving power of the inventive polyglycerol partial esters, these were mixed with cosmetic oils and treated with water. The oils tested were avocado oil (supplier: Gustav Heess) and caprylic/capric triglycerides (TEGOSOFT® CT, Evonik Industries AG). The proportion of solubilizer required to completely dissolve 0.5% of the respective oil in water was investigated. For this purpose, the solubilizer (various amounts) was thoroughly mixed with the oil (0.5 g) and then slowly treated with water (made up to 100 g) with stirring. The mixture was stirred for one hour at 45° C. After cooling to 20° C., a "clear mixture" must not become turbid again over a period of 1 week.

In Table 1, the resulting mass ratios of solubilizer to oil which were required to obtain clear mixtures are summarized.

TABLE 1

Solubilizer-to-oil ratio required for a clear solution of the oil in water.

|  | Avocado oil | Caprylic/capric triglycerides |
|---|---|---|
| Polyglycerol partial ester A | 10:1 | 4:1 |
| Polyglycerol partial ester E | 8:1 | 4:1 |
| Polyglycerol partial ester F | 9:1 | 4:1 |
| Polyglycerol partial ester G | 11:1 | 5:1 |
| Polyglycerol partial ester H (non-inventive) | >20:1 | 9:1 |
| TEGOSOFT® PC 41 (non-inventive) | >20:1 | 16:1 |
| TAGAT® CH 40 (non-inventive) | 6:1 | 6:1 |

It is evident from the results in Table 1 that the inventive polyglycerol partial esters A, E, F and G have distinctly better solubilizing properties than the polyether-free comparative examples polyglycerol partial ester H and TEGOSOFT® PC 41. Surprisingly, similar solubilizer-to-oil ratios are even achieved as with the polyether-containing standard solubilizer TAGAT® CH 40 and whose performance is to some extent even exceeded.

Example 5

Improved Dissolving Power of the Inventive Polyglycerol Partial Esters in Surfactant Formulations in Comparison to the Non-Inventive Polyglycerol Partial Esters In addition to the dissolving properties of the inventive polyglycerol partial esters for oil in water shown in example 4, the dissolving power for oils in surfactant formulations was also investigated.

For this purpose, the respective solubilizer was mixed with 0.5 g of caprylic/capric triglycerides (TEGOSOFT® CT, Evonik Industries AG) at 60° C. for 5 min. The water was then slowly added at 60° C. with stirring and the mixture was stirred for 10 min. The mixture was then cooled to 30° C. over a period of 30 min. The mixture was then treated with the surfactants with stirring.

The proportion of solubilizer required to completely dissolve 0.5% of the oil in the respective surfactant system was investigated. Two surfactant systems were used: a standard lauryl ether sulphate/betaine mixture (Table 2) and a polyether-free formulation (Table 3). In Table 4, the resulting mass ratios of solubilizer-to-oil which were required to obtain clear mixtures are summarized.

TABLE 2

Formulation Y for assessment of the solubilizing properties in a standard surfactant system.

| Solubilizer | X % |
|---|---|
| TEGOSOFT® CT, Evonik Industries AG, (INCI: Caprylic/capric triglycerides) | 0.5% |
| Water | to 100.0% |
| Texapon® NSO, BASF Cognis, 28%, (INCI: Sodium laureth sulphate | 32.0% |
| TEGO® Betaine F 50, Evonik Industries AG, 38%, (INCI: Cocamidopropyl betaine) | 8.0% |
| Polymer JR 400, Amerchol, (Polyquaternium-10) | 0.2% |
| Citric acid, 30% | to pH 5.5 |

TABLE 3

Formulation Z for assessment of the solubilizing properties in a polyether-free surfactant system.

| Solubilizer | X % |
|---|---|
| TEGOSOFT® CT, Evonik Industries AG, (INCI: Caprylic/capric triglycerides) | 0.5% |
| Water | to 100.0% |
| REWOTERIC® AM C, Evonik Industries AG, 32%, (INCI: Sodium cocoamphoacetate) | 17.5% |
| Plantacare 1200 UP, BASF Cognis, 50%, (INCI: Lauryl glucoside) | 8.8% |
| Plantacare 818 UP, BASF Cognis, 51%, (INCI: Coco glucoside) | 2.4% |
| PERLASTAN® SC 25 NKW, Schill&Seilacher, 25%, (Disodium/sodium cocoyl glutamate) | 14.4% |
| Citric acid, 30% | to pH 5.2 |

TABLE 4

Solubilizer-to-oil ratio required for a clear solution of TEGOSOFT ® CT in the surfactant formulations.

|  | TEGOSOFT ® CT in formulation Y | TEGOSOFT ® CT in formulation Z |
|---|---|---|
| Polyglycerol partial ester A | 6:1 | 8:1 |
| Polyglycerol partial ester F | 5:1 | 6:1 |
| NATRAGEM ® S 150 NP-LQ-(CM) (non-inventive) | 12:1 | 11:1 |
| TEGOSOFT ® PC 41 (non-inventive) | 12:1 | 14:1 |
| TAGAT ® CH 40 (non-inventive) | 8:1 | 5:1 |

The results in Table 4 show that the inventive polyglycerol partial esters A and F have distinctly improved solubilizer properties in comparison to the comparative products NATRAGEM® S 150 NP-LQ-(CM) and TEGOSOFT® PC 41. Surprisingly, better results were also obtained to some extent with the inventive polyglycerol partial esters A and F than with the polyether-containing product TAGAT® CH 40.

Example 6

Improved Skin Care Power and Foam Properties of the Inventive Polyglycerol Partial Esters in Surfactant Mixtures in Comparison to Non-Inventive Polyglycerol Partial Esters To evaluate the skin care benefit and the foam properties of the inventive polyglycerol partial ester G in aqueous surfactant formulations, a sensory handwashing test was conducted in comparison to the comparative example TEGOSOFT® PC 41 according to the prior art.

A group consisting of 10 trained test personnel washed their hands in a defined manner and assessed foam properties and skin feel using a grading scale from 1 (poor) to 5 (very good).

The products were tested in each case in a standardized surfactant formulation, using the standard surfactant system of 9% active sodium laureth sulphate and 3% active cocamidopropyl betaine (Table 5).

TABLE 5

Test formulations for the handwashing test:

| Formulation examples | U | V | W |
|---|---|---|---|
| Texapon ® NSO-IS, BASF Cognis, 28%, (INCI: Sodium laureth sulphate) | 32.0% | 32.0% | 32.0% |
| TEGO ® Betaine F 50, Evonik Industries AG, 38%, (INCI: Cocamidopropyl betaine) | 8.0% | 8.0% | 8.0% |
| NaCl | 1.5% | 1.5% | 1.5% |
| Citric acid | 0.2% | 0.2% | 0.2% |
| Water, demineralized | 58.3% | 55.3% | 55.3% |
| Polyglycerol partial ester G (inventive) | — | 3.0% | — |
| TEGOSOFT ® PC 41 (non-inventive) | — | — | 3.0% |

The sensory test results are summarized in Table 6.

TABLE 6

Results of the handwashing test:

| Test formulation | U | V | W |
|---|---|---|---|
| Foaming behaviour | 3.3 | 3.6 | 3.5 |
| Foam volume | 3.1 | 3.3 | 3.2 |
| Foam creaminess | 2.9 | 4.1 | 3.7 |
| Skin feel during washing | 2.9 | 3.1 | 3.0 |
| Rinseability | 3.3 | 3.8 | 3.7 |
| Skin smoothness | 2.1 | 2.8 | 2.4 |
| Skin softness | 2.3 | 3.1 | 2.8 |
| Skin smoothness after 3 min | 3.1 | 3.8 | 3.6 |
| Skin softness after 3 min | 2.9 | 3.7 | 3.4 |

It is evident from the test results in Table 6 that the inventive formulation V using the inventive polyglycerol partial ester G is superior, surprisingly, in all application properties in comparison to the comparative formulation W according to the prior art. In this light, the results of the inventive formulation V can be designated as very good and show a distinct improvement compared to the prior art.

It is evident from the measurements that the inventive polyglycerol partial ester G in formulation V led especially to a significant improvement specifically of the foam creaminess and also the skin smoothness and the skin softness.

Further Formulation Examples

The formulation examples given in the tables below show exemplary representatives of a large number of possible compositions according to the invention.

If the preparation of the formulation requires the separate preparation or mixing of formulation constituents beforehand, this is termed multiphase preparation. If a two-phase preparation is required, the two phases are labelled A and B in the stated tables. In the case of three- or more-phase processes, the phases are called A, B, C etc. Unless stated otherwise, the data in the tables are data in % by weight. In the following formulation examples, the data or % by weight are based on the respective active substance. Some products, however, are commercially available as solutions, especially in water, such that in these cases more of the commercial products were used accordingly, depending on the active content.

"Product example A to G" corresponds to the "polyglycerol partial esters A to G of example 1".

TABLE 7

| Formulation for Wet Wipes | |
|---|---|
| Butylene glycol | 2.0% |
| Glycerol | 1.0% |
| Product example A | 1.0% |
| Silicone quaternium-22; Polyglycerol-3 caprate; Dipropylene glycol; Cocamidopropyl betaine | 0.5% |
| Allantoin | 0.2% |
| Maltodextrin | 0.5% |
| Chamomilla extract | 0.1% |
| Phenoxyethanol; Ethylhexyl glycerol | 0.7% |
| Perfume | q.s. |
| Water | to 100.0% |
| Citric acid, 30% | to pH 5.5 |

TABLE 8

Bath cream

| | |
|---|---|
| Water | to 100.0% |
| Sodium laureth sulphate | 8.0% |
| Coco glucoside | 4.0% |
| Cocamidopropyl betaine | 5.0% |
| Product example B | 1.0% |
| PEG-18 Glyceryl oleate/cocoate | 2.0% |
| PEG-40 Sorbitan peroleate | 1.4% |
| Perfume (fragrance) | 0.2% |
| *Argania spinosa* kernel oil | 0.2% |
| *Citrus aurantifolia* (lime) oil | 0.2% |
| Linalool | 0.1% |
| Coumarin | 0.1% |
| Glycerol | 0.5% |
| Glycol distearate | 0.5% |
| Styrene/acrylates copolymer | 0.2% |
| Tocopherol | 0.1% |
| Preservative | q.s. |
| Citric Acid | to pH 5.2 |

TABLE 9

Shower cream

| | |
|---|---|
| Water | to 100.0% |
| Glycerol | 4.0% |
| Sodium laureth sulphate | 4.0% |
| Cocamidopropyl betaine | 3.5% |
| Product example G | 2.0% |
| Coco glucoside | 2.0% |
| *Ricinus communis* seed oil seed) | 0.5% |
| Glyceryl oleate | 0.5% |
| *Argania spinosa* kernel oil | 0.1% |
| *Butyrospermum parkii* butter extract | 0.1% |
| Limonene | 0.1% |
| Perfume (fragrance) | 0.2% |
| Acrylates/C10-30 alkyl acrylate crosspolymer | 0.2% |
| Hydroxypropyl methylcellulose | 0.2% |
| Styrene/acrylates copolymer | 0.2% |
| Sodium hydroxide | 0.2% |
| Glycol distearate | 0.4% |
| Silica | 0.2% |
| Tocopherol | 0.1% |
| Preservative | q.s. |
| Citric acid | to pH 5.2 |

TABLE 10

Shower oil

| | |
|---|---|
| *Helianthus annuus* seed oil | 10.0% |
| *Ricinus communis* seed oil | 10.0% |
| MIPA-Laureth sulphate | 20.0% |
| Product example A | 15.0% |
| Laureth-4 | 0.5% |
| Cocamide DEA | 0.9% |
| Perfume (fragrance) | 0.2% |
| *Prunus amygdalus dulcis* oil | 0.8% |
| *Argania spinosa* kernel oil | 0.8% |
| Water | 0.5% |
| Preservative | q.s. |
| Citric acid | to pH 5.5 |

TABLE 11

Bath oil

| | |
|---|---|
| Water | to 100.0% |
| Sodium laureth sulphate | 7.0% |
| Cocamidopropyl betaine | 6.0% |
| Cocamide DEA | 2.5% |
| Sodium trideceth sulphate | 2.2% |
| Product example E | 2.0% |
| Perfume (fragrance) | 0.5% |
| PEG-40 Hydrogenated castor oil | 0.1% |
| Trideceth-9 | 0.2% |
| Sodium lauroamphoacetate | 0.5% |
| Benzophenone-4 | 0.2% |
| Cocamide MEA | 0.4% |
| Propylene glycol | 0.5% |
| Disodium EDTA | 0.1% |
| Sodium chloride | 0.5% |
| Glycerol | 0.4% |
| Benzyl alcohol | 0.4% |
| *Argania spinosa* oil | 0.2% |
| Sodium cocoyl glutamate | 0.3% |
| Phenoxyethanol | 0.2% |
| Xanthan gum | 0.2% |
| Carbomer | 0.2% |
| Lactic acid | 0.3% |
| Magnesium chloride | 0.1% |
| Coumarin | 0.1% |
| Citric acid | to pH 5.2 |
| Preservative | q.s. |

TABLE 12

Shower cream

| | |
|---|---|
| Water | to 100.0% |
| Sodium laureth sulphate | 10.0% |
| Glycerol | 3.0% |
| Cocamidopropyl betaine | 3.0% |
| Product example F | 2.0% |
| Decyl glucoside | 1.5% |
| Perfume | q.s. |
| *Glycine soya* oil | 0.2% |
| *Helianthus annuus* seed oil | 0.1% |
| Lecithin | 0.2% |
| Coco glucoside | 0.5% |
| Glyceryl oleate | 0.3% |
| Coumarin | 0.1% |
| Preservative | q.s. |

TABLE 13

Body shampoo

| | | |
|---|---|---|
| Phase A | Product example F | 3.0% |
| | *Simmondsia chinensis* (jojoba) seed oil | 0.7% |
| | Perfume | 0.2% |
| Phase B | Sodium cocoamphoacetate | 4.0% |
| Phase C | Water | to 100.0% |
| | Acrylates/C10-30 alkyl acrylate crosspolymer | 0.9% |
| Phase D | Sodium lauroyl methyl isethionate | 4.0% |
| | Capryl/capramidopropyl betaine | 2.0% |
| | Citric acid | 1.3% |
| Phase E | Water | 10.0% |
| | Polyquaternium-7 | 0.3% |
| | Preservative | q.s. |

TABLE 14

Body shampoo

| | | |
|---|---|---|
| Phase A | Product example C | 6.5% |
| | *Simmondsia chinensis* (jojoba) seed oil | 0.4% |
| | Perfume | 0.2% |
| Phase B | Water | to 100.0% |
| Phase C | Sodium cocoamphoacetate | 4.0% |

TABLE 14-continued

Body shampoo

| | | |
|---|---|---|
| Phase D | Water | 30.0% |
| | Acrylates/beheneth-25 methacrylate copolymer | 2.0% |
| | Sodium lauroyl methyl isethionate | 4.0% |
| | Disodium lauryl sulphosuccinate | 2.0% |
| Phase E | Preservative | q.s. |

TABLE 15

Shampoo

| | | |
|---|---|---|
| Phase A | Product example E | 3.0% |
| | Caprylic/capric triglyceride | 0.5% |
| | Perfume | 0.2% |
| Phase B | Water | to 100.0% |
| Phase C | Sodium cocoamphoacetate | 7.0% |
| Phase: | Glycerol | 1.0% |
| | Xanthan gum | 0.8% |
| | Water | 25.0% |
| Phase E | Water | 10.0% |
| | Acrylates/beheneth-25 methacrylate copolymer | 2.0% |
| Phase F | Water | 10.0% |
| | Polyquaternium-10) | 0.2% |
| Phase G | Cocamidopropyl betaine | 5.0% |
| | Preservative | q.s. |

TABLE 16

Shampoo

| | | |
|---|---|---|
| Phase A | Product example E | 8.0% |
| | *Argania spinosa* kernel Oil | 0.5% |
| Phase: | Water | to 100.0% |
| Phase C | Perfume | 0.3% |
| | Polyglyceryl-6 caprylate; Polyglyceryl-4 caprate; Propylene glycol | 2.0% |
| Phase D | Water | 20.0% |
| Phase E | Sodium laureth sulphate | 9.0% |
| Phase F | Water | 10.0% |
| | Cocamidopropyl betaine | 3.0% |
| | PEG-120 methyl glucose dioleate | 1.0% |
| Phase G | Water | 10.0% |
| | Sodium chloride | 0.7% |
| | Polyquaternium-10 | 0.2% |
| Phase H | Citric acid | to pH 5.5 |
| Phase I | Preservative | q.s. |

TABLE 17

Shower gel

| | | |
|---|---|---|
| Phase: | Product example F | 3.0% |
| | Caprylic/capric triglyceride | 0.5% |
| | Perfume | 0.2% |
| Phase B | Water | to 100.0% |
| Phase C | Sodium cocoamphoacetate | 5.6% |
| Phase D | Lauryl glucoside | 4.4% |
| Phase E | Coco glucoside | 1.2% |
| Phase F | Sodium/disodium cocoyl glutamate | 3.6% |
| Phase G | Water | 10.0% |
| | Glycerol | 0.7% |
| | Water | 10.0% |
| | Xanthan gum | 2.0% |
| Phase H | Citric acid | to pH 6.0 |
| Phase I | Preservative | q.s. |

TABLE 18

Shampoo

| | | |
|---|---|---|
| Phase: | Product example C | 2.0% |
| | Caprylic/capric triglyceride | 0.5% |
| | Perfume | 0.2% |
| Phase B | Water | to 100.0% |
| Phase C | Sodium lauryl sulphate | 9.0% |
| Phase: | Cocamidopropyl betaine | 3.0% |
| Phase E | Cocamide MEA | 1.9% |
| | Xanthan gum | 0.2% |
| | Water | 10.0% |
| Phase F | Water | 10.0% |
| | Polyquatemium-10 | 0.2% |
| Phase: | Citric acid | to pH 5.7 |
| Phase H | Preservative | q.s. |

TABLE 19

Deo

| | | |
|---|---|---|
| Phase A | Product example E | 3.0% |
| | *Glycine soja* (soybean) oil | 0.2% |
| | Perfume | 0.1% |
| Phase B | Phenoxyethanol | 0.5% |
| | Caprylyl glycol | 0.2% |
| Phase C | Water | 50.0% |
| | Hydroxyethyl cellulose | 0.75% |
| | Sodium hydroxide (10% in water) | 0.25% |
| Phase D | Aluminium chlorohydrate | 19.0% |
| Phase E | Water | to 100.0% |

TABLE 20

Cleansing Oil Shampoo

| | |
|---|---|
| Water | to 100.0% |
| Sodium laureth sulphate | 7.0% |
| MIPA-Laureth sulphate | 4.0% |
| Sodium chloride | 3.2% |
| Cocamidopropyl betaine | 3.0% |
| Product example E | 3.0% |
| Glycerol | 2.5% |
| PEG-18 Castor oil dioleate | 2.0% |
| Propylene glycol; PEG-55 Propylene glycol oleate | 2.0% |
| Laureth-5 carboxylic acid | 1.0% |
| *Persea gratissima* (avocado) oil | 1.0% |
| Polyglyceryl-6 caprylate; Polyglyceryl-4 caprate; Propylene glycol | 0.9% |
| Sodium benzoate | 0.7% |
| Salicylic acid | 0.3% |
| Linalool | 0.2% |
| alpha-Isomethyl ionone | 0.1% |
| Limonene | 0.1% |
| *Zea mays* (corn) germ oil | 0.2% |
| *Argania spinosa* oil | 0.1% |
| *Camellia oleifera* seed oil | 0.1% |
| Sodium hydroxide | 0.3% |
| Citric acid | to pH 5.0 |
| Perfume, Dyes | q.s. |

TABLE 21

Pampering Oil Bath

| | |
|---|---|
| Water | to 100% |
| *Glycine soya* oil | 20.0% |
| Product example B | 10.0% |
| Polyglyceryl-3 palmitate | 4.5% |
| Glyceryl caprylate | 4.5% |
| *Simmondsia chinensis* seed oil | 1.5% |
| *Prunus amygdalus dulcis* (sweet almond) oil | 1.0% |
| *Triticum vulgare* germ oil | 1.0% |
| Tocopherol | 0.2% |

TABLE 21-continued

Pampering Oil Bath

| | |
|---|---|
| Limonene | 0.1% |
| Linalool | 0.1% |
| Citral | 0.1% |
| Dyes | q.s. |

TABLE 22

Shower Cream

| | |
|---|---|
| Water | to 100% |
| Glycerol | 7.5% |
| *Glycine* soya oil | 3.0% |
| Lauryl glucoside | 3.0% |
| Sodium coco sulphate | 3.0% |
| Product example C | 2.5% |
| Alcohol | 1.5% |
| Xanthan gum | 1.5% |
| *Butyrospermum parkii* butter extract | 1.2% |
| Sodium cetearyl sulphate | 1.0% |
| Sodium cocoyl glutamate | 1.0% |
| Disodium cocoyl glutamate | 1.0% |
| Tocopherol | 0.1% |
| *Helianthus annuus* seed oil | 0.3% |
| Limonene | 0.1% |
| Benzyl salicylate | 0.1% |
| Linalool | 0.1% |
| Dyes | q.s. |

TABLE 23

Shower Gel

| | |
|---|---|
| Water | to 100% |
| Sodium coco sulphate | 5.0% |
| Glycerol | 5.0% |
| Lauryl glucoside | 4.0% |
| Sodium lactate | 2.5% |
| Product example D | 2.0% |
| Polyglyceryl-4 caprate | 2.0% |
| Sodium cocoyl glutamate | 2.0% |
| Disodium cocoyl glutamate | 2.0% |
| Alcohol | 1.0% |
| *Prunus cerasus* fruit extract | 1.0% |
| Polyglyceryl-6 caprylate; Polyglyceryl-4 caprate; Propylene glycol | 1.0% |
| Limonene | 0.1% |
| Coumarin | 0.2% |
| Linalool | 0.1% |
| Citral | 0.1% |
| Dyes | q.s. |

TABLE 24

Liquid Soap

| | |
|---|---|
| Water | to 100% |
| Glycerol | 7.0% |
| Alcohol | 4.0% |
| Sodium coco sulphate | 3.0% |
| Lauryl glucoside | 2.5% |
| Product example E | 2.0% |
| Xanthan gum | 1.5% |
| *Mangifera indica* (mango) fruit extract | 0.7% |
| Limonene | 0.1% |
| Linalool | 0.1% |
| Dyes | q.s. |

TABLE 25

Shampoo for Children

| | |
|---|---|
| Water | to 100% |
| Sodium coco sulphate | 7.0% |
| Decyl glucoside | 5.0% |
| Lactis Proteinum | 3.5% |
| Sorbitan caprylate | 3.0% |
| Product example F | 3.0% |
| Glycerol | 2.5% |
| Sodium lactate | 2.5% |
| Alcohol | 2.0% |
| Hydrolysed wheat protein | 0.7% |
| Hydrolysed wheat starch | 0.7% |
| Sodium chloride | 0.9% |
| Limonene | 0.1% |
| Citral | 0.1% |
| Phenethyl alcohol | 0.1% |
| Dyes | q.s. |

TABLE 26

Cream Soap

| | |
|---|---|
| Water | to 100% |
| Alcohol | 5.0% |
| Coco glucoside | 5.0% |
| Glycerol | 5.0% |
| Product example F | 2.5% |
| Disodium cocoyl glutamate | 2.0% |
| Xanthan gum | 1.5% |
| Citric acid | to pH 5.5 |
| *Malva sylvestris* leaf extract | 1.0% |
| Glyceryl oleate | 1.0% |
| Sodium cocoyl glutamate | 0.7% |
| Linalool | 0.1% |
| Limonene | 0.1% |
| Dyes | q.s. |

TABLE 27

Make-up Remover

| | |
|---|---|
| Sodium cocoamphopropionate | 5.0% |
| Propylene glycol | 35.0% |
| Product example F | 30.0% |
| Glycerol | 30.0% |
| Preservative | q.s. |

TABLE 28

Make-up Remover

| | |
|---|---|
| Cocamidopropyl betaine | 8.0% |
| Water | 79.0% |
| Product example E | 3.0% |
| Glycerol | 10.0% |
| Citric acid | to pH 5.5 |
| Preservative | q.s. |

TABLE 29

Solution for Wet Wipes

| | |
|---|---|
| Product example E | 1.5% |
| Perfume | 0.2% |
| Glycerol | 2.0% |
| Sodium lactate; Sodium PCA; Glycine; Fructose; Urea; Niacinamide; Inositol; Sodium benzoate; Lactic acid | 0.2% |
| Water | 95.6% |
| Preservative | q.s. |

TABLE 30

Solution for Wet Wipes

| | |
|---|---|
| Product example E | 2.0% |
| Isopropyl myristate | 0.3% |
| Phenoxyethanol; Methylparaben; Ethylparaben; Butylparaben; Propylparaben; Isobutylparaben | 0.2% |
| Perfume | 0.1% |
| Propylene glycol | 3.0% |
| Water | 94.0% |
| Cetrimonium bromide | 0.1% |

TABLE 31

O/W Make-up remover wipe

| | | |
|---|---|---|
| Phase A | Ethylhexyl stearate; Phenoxyethanol; Polyglyceryl-4 laurate; Sorbitan laurate; Dilauryl citrate | 4.0% |
| | Cetyl ricinoleate | 0.8% |
| Phase B | Water | to 100.0% |
| | Glycerol | 1.5% |
| Phase C | Product example C | 1.0% |
| Phase D | Phenoxyethanol | 0.1% |
| | Perfume | q.s. |
| | Preservative | q.s. |

TABLE 32

Micellar water

| | |
|---|---|
| Water | to 100.0% |
| Product example D | 5.0% |
| Glycerol | 1.5% |
| Disodium cocoamphodiacetate | 0.5% |
| Disodium EDTA | 0.2% |
| Polyaminopropyl biguanide | 0.2% |
| Citric acid, 30% | to pH 5.5 |

TABLE 33

Micellar Solution Cleanser

| | |
|---|---|
| Water | to 100.0% |
| Butylene glycol | 5.0% |
| Coco glucoside | 2.0% |
| Product example D | 2.0% |
| Glycerol | 1.0% |
| Allantoin | 0.1% |
| Cistus incanus extract; Maltodextrin | 0.2% |
| Perfume | 0.2% |
| Citric acid, 30% | to pH 5.5 |

TABLE 34

Cleansing Water

| | |
|---|---|
| Water | to 100.0% |
| Product example E | 2.5% |
| Phenoxyethanol; Ethylhexylglycerol | 0.9% |
| Caprylic/capric triglyceride | 0.5% |
| Glycerol | 0.5% |
| Disodium EDTA | 0.2% |
| Citric acid, 30% | to pH 5.5 |

TABLE 35

Shower Crème

| | |
|---|---|
| Water | to 100% |
| Ammonium lauryl sulphate | 10.0% |
| Product example D | 2.0% |
| Aloe barbadensis leaf juice | 2.0% |
| Cocamidopropyl betaine | 2.0% |
| Decyl glucoside | 1.0% |
| Glycerol | 1.0% |
| Prunus amygdalus dulcis oil | 0.5% |
| Glyceryl oleate | 0.3% |
| Lauryl glucoside | 0.3% |
| Coco glucoside | 0.4% |
| Benzyl alcohol | 0.2% |
| Benzoic acid | 0.3% |
| Dehydroacetic acid | 0.2% |
| Sodium benzoate | 0.3% |
| Potassium sorbate | 0.2% |
| Tocopherol | 0.1% |
| Citric acid | to pH 4.5 |
| Perfume, Dyes | q.s. |

TABLE 36

Shower Crème

| | |
|---|---|
| Water | to 100% |
| Sodium laureth sulphate | 8.0% |
| Product example F | 3.0% |
| Cocamidopropyl betaine | 3.0% |
| Glycerol | 1.0% |
| Glucose | 0.5% |
| Prunus amygdalus dulcis oil | 0.7% |
| Sodium chloride | 0.3% |
| Polyquaternium-7 | 0.3% |
| Styrene/acrylates copolymer | 0.4% |
| PEG-200 Hydrogenated glyceryl palmate; PEG-7 Glyceryl cocoate | 0.5% |
| Citric acid | to pH 5.5 |
| Perfume, Dyes | q.s. |

TABLE 37

Care shower

| | |
|---|---|
| Water | to 100% |
| Sodium laureth sulphate | 9.0% |
| Sodium hydroxypropyl starch phosphate | 2.5% |
| Product example E | 2.0% |
| Cocamidopropyl betaine | 2.0% |
| Petrolatum | 1.0% |
| Sodium cocoyl glycinate | 1.0% |
| Lauric acid | 0.5% |
| Sodium lauroyl isethionate | 0.5% |
| Glycerol | 0.4% |
| Helianthus annuus seed oil | 0.3% |
| Olea europaea fruit oil | 0.2% |
| Sodium chloride | 0.4% |
| Stearic acid | 0.5% |
| Guar hydroxypropyltrimonium chloride | 0.2% |
| Sodium Cocoyl isethionate | 0.1% |
| Tetrasodium EDTA | 0.1% |
| Alumina | 0.1% |
| Citric acid | to pH 5.5 |
| Perfumes, Dyes, Preservatives | q.s. |

TABLE 38

Shower Crème

| | |
|---|---|
| Water | to 100% |
| Sodium coco sulphate | 15.0% |
| Glycerol | 3.5% |

TABLE 38-continued

Shower Crème

| | |
|---|---|
| Product example F | 3.5% |
| Glycine soya oil | 0.5% |
| Coco glucoside | 0.8% |
| Caprylic/capric triglyceride | 0.2% |
| Xanthan gum | 0.8% |
| *Prunus amygdalus dulcis* oil | 0.1% |
| *Simmondsia chinensis* seed oil | 0.1% |
| Sodium cocoyl glutamate | 0.3% |
| Disodium cocoyl glutamate | 0.5% |
| Sodium cetearyl sulphate | 0.2% |
| Tocopherol | 0.1% |
| *Helianthus annuus* seed oil | 0.1% |
| Alcohol | 0.5% |
| Citral | 0.1% |
| Geraniol | 0.1% |
| Limonene | 0.1% |
| Linalool | 0.1% |
| Citric acid | to pH 5.8 |
| Perfume, Dyes | q.s. |

TABLE 39

Further formulation examples

| | 39a | 39b | 39c | 39d | 39e | 39f | 39g | 39h | 39i | 39j |
|---|---|---|---|---|---|---|---|---|---|---|
| Water | | | | | to 100% | | | | | |
| Product example D | 3.0% | 4.0% | 5.5% | 1.0% | 3.0% | 3.0% | 5.0% | 4.0% | 3.5% | 3.0% |
| Sodium laureth sulphate | 9.0% | 8.0% | 9.0% | — | — | — | — | — | — | — |
| Sodium lauryl sulphate | — | — | — | 6.0% | — | — | — | — | 3.5% | — |
| Cocamidopropyl betaine | — | 2.0% | 3.0% | 7.0% | 5.0% | 6.0% | — | — | 2.0% | 7.0% |
| Sodium cocoamphoacetate | 3.0% | — | — | 1.5% | 4.5% | — | 3.0% | — | 3.5% | — |
| Lauryl glucoside | — | — | — | — | 3.5% | 5.0% | 3.0% | 7.0% | — | — |
| Coco glucoside | — | 2.0% | — | — | 1.5% | 1.0% | 5.5% | 2.5% | 2.0% | — |
| Sodium cocoyl glutamate | — | — | — | — | — | 1.0% | 1.7% | 5.0% | 0.5% | — |
| Stearic acid | — | — | 1.0% | — | — | — | — | — | 0.1% | 3.5% |
| Glyceryl glucoside | — | 0.3% | — | — | 0.3% | — | 0.2% | — | — | — |
| Sucrose cocoate | 0.5% | — | 1.0% | 1.0% | 0.3% | 0.2% | — | 1.0% | 1.0% | 1.0% |
| Glycerol | 0.5% | 1.0% | 0.5% | — | 0.3% | 0.4% | 1.5% | 1.0% | 0.5% | 1.0% |
| PEG-7 Glyceryl cocoate | — | 0.3% | — | — | — | — | — | — | — | 0.5% |
| Trideceth-9 | — | 0.2% | — | — | 0.2% | — | — | — | — | — |
| Polysorbate 20 | — | — | 0.5% | — | — | — | — | — | 0.3% | 0.2% |
| PEG-40 Hydrogenated castor oil | — | — | 0.3% | — | 0.5% | — | — | — | 1.0% | — |
| PEG-6 Caprylic/capric glycerides | — | — | — | — | 0.3% | — | — | — | 0.2% | 0.2% |
| Polyglyceryl-4 caprate | — | — | — | 2.0% | — | 0.5% | — | 0.5% | — | 0.5% |
| Polyquaternium-10 | — | 0.2% | — | 0.1% | — | — | — | 0.2% | 0.2% | — |
| Hydroxypropyl guar hydroxypropyltrimonium chloride | 0.2% | — | 0.3% | 0.2% | 0.2% | 0.2% | 0.2% | 0.1% | — | — |
| Silicone quaternium-22 | — | — | 0.3% | — | 0.3% | — | — | — | — | — |
| Dimethicone | — | 0.3% | — | — | — | — | — | — | 0.1% | — |
| Amodimethicone | — | 0.1% | — | 0.1% | 0.1% | — | — | — | 0.5% | — |
| *Argania spinosa* oil | — | — | 0.2% | 0.1% | 0.1% | — | 0.2% | — | — | — |
| *Prunus amygdalus dulcis* oil | 0.2% | — | 0.2% | 0.3% | — | 0.1% | — | — | 0.2% | 0.2% |
| *Olea europaea* fruit oil | 0.2% | 0.1% | — | — | — | 0.1% | — | 0.2% | 0.1% | — |
| *Butyrospermum parkii* butter extract | — | — | 0.2% | — | 0.1% | — | — | — | — | — |
| *Persea gratissima* oil | — | — | — | 0.1% | — | 0.1% | 0.2% | — | — | — |
| Hydrogenated castor oil | — | 0.2% | — | 0.1% | — | — | — | — | 0.1% | 0.2% |
| Glycol distearate | — | 0.5% | — | — | 0.5% | — | 0.3% | — | 0.5% | 0.5% |
| Isostearamide MIPA; Glyceryl laurate | 1.0% | — | — | 1.5% | — | — | 0.2% | — | 1.0% | 0.5% |
| Cocamide DEA | — | — | 0.5% | — | — | 1.0% | — | — | — | — |
| Sodium chloride | 0.3% | 1.2% | 1.0% | 0.5% | — | 1.0% | — | 1.0% | — | 0.3% |
| PEG-120 Methyl glucose dioleate | 0.2% | 3.5% | 1.0% | — | 1.5% | — | — | — | 0.5% | — |
| Xanthan gum | — | — | 0.5% | 0.8% | — | 0.7% | 2.0% | 1.0% | — | — |
| Cellulose | — | — | — | 0.1% | — | 0.1% | 0.1% | 0.2% | 0.1% | — |
| Zinc pyrithione | — | 0.1% | — | — | — | — | — | — | 0.1% | — |
| Benzophenone-4 | — | 0.1% | 0.1% | 0.1% | 0.1% | — | 0.1% | — | — | — |
| Tetrasodium EDTA | 0.1% | 0.1% | — | 0.1% | 0.1% | — | — | — | 0.1% | — |
| Caffeine | — | 0.1% | 0.1% | — | — | — | — | 0.1% | 0.1% | — |
| Hydrolysed keratin | — | — | 0.1% | — | — | 0.1% | 0.2% | 0.1% | 0.1% | — |
| Panthenol | 0.1% | 0.1% | 0.1% | 0.1% | 0.1% | 0.1% | — | 0.1% | 0.1% | 0.1% |
| Citric acid | | | | | to pH 5.5 | | | | | |
| Perfumes, Dyes, Preservatives | | | | | q.s. | | | | | |

TABLE 40

Further formulation examples

| | 40a | 40b | 40c | 40d | 40e | 40f | 40g | 40h | 40i | 40j |
|---|---|---|---|---|---|---|---|---|---|---|
| Water | | | | | to 100% | | | | | |
| Product example F | 9.0% | 5.0% | 5.0% | 4.0% | 4.0% | 2.5% | 6.0% | 4.0% | 3.0% | 3.0% |
| Sodium lauryl sulphate | — | 8.0% | 8.0% | — | — | — | — | 3.5% | — | — |
| Coco betaine | — | 5.0% | — | 5.5% | — | — | — | 3.0% | — | — |
| Cocamidopropyl betaine | — | — | 3.0% | — | 5.0% | — | — | — | 3.0% | 2.0% |
| Sodium cocoamphoacetate | — | — | 2.5% | 3.0% | — | 5.0% | — | 3.0% | 4.0% | — |
| Disodium lauryl sulphosuccinate | — | — | 1.0% | — | — | — | — | 1.2% | — | — |
| Coco glucoside | — | — | — | 3.0% | 5.0% | 4.0% | 5.0% | 1.0% | — | 2.0% |
| Sodium cocoyl glutamate | — | — | — | 2.5% | — | 3.0% | 4.5% | 0.5% | 2.5% | 0.3% |
| Stearic acid | — | — | 0.3% | — | — | — | — | 0.1% | — | 0.5% |
| Sodium cocoyl glycinate | — | — | — | — | 5.0% | — | 3.5% | — | 2.0% | 7.0% |
| Sodium lauroyl methyl isethionate | — | — | — | 1.0% | — | 1.5% | — | 1.0% | 0.5% | 0.5% |
| Sucrose cocoate | 0.5% | 0.4% | — | 1.0% | — | — | 0.2% | 0.3% | 1.0% | 0.3% |
| Glycerol | 1.5% | 0.3% | 0.5% | 0.5% | 0.3% | 0.5% | 1.0% | 0.5% | 0.3% | 1.0% |
| PEG-40 Hydrogenated castor oil | — | 1.0% | — | — | — | — | — | 0.3% | — | — |
| Polyglyceryl-4 caprate | 0.5% | — | — | 0.5% | — | 2.6% | — | — | 1.1% | — |
| Polyquaternium-11 | — | 0.2% | — | — | 0.1% | — | — | 0.2% | — | 0.3% |
| Guar hydroxypropyltrimonium chloride | — | — | 0.3% | 0.2% | 0.2% | 0.3% | 0.2% | 0.1% | 0.2% | — |
| Dimethicone | — | 0.3% | — | — | — | — | — | 0.2% | — | — |
| Aminopropyl dimethicone | — | 0.3% | 0.5% | — | — | — | — | 0.3% | — | — |
| *Helianthus annuus* seed oil | 0.3% | — | 0.1% | 0.5% | — | 0.1% | 0.1% | 0.2% | — | 0.1% |
| *Olea europaea* fruit oil | 0.2% | 0.1% | 0.2% | — | 0.2% | 0.1% | 0.2% | — | 0.6% | 0.2% |
| PEG-3 distearate | — | 0.5% | — | — | — | — | — | 0.5% | — | — |
| Acrylates/C10-30 alkyl acrylate crosspolymer | 0.5% | — | 0.4% | — | 0.5% | 0.4% | — | — | 0.5% | — |
| Sodium hydroxide, 25% | 0.6% | — | 0.6% | — | 0.8% | 0.5% | — | — | 0.7% | — |
| Cocamide MEA | — | 0.8% | 1.0% | 1.0% | — | 0.2% | 0.6% | 1.0% | — | 0.3% |
| Sodium chloride | 0.2% | 0.7% | 0.2% | — | 0.2% | 0.1% | — | 1.0% | 0.2% | 1.0% |
| Propylene glycol; PEG-55 Propylene glycol oleate | — | 2.5% | — | — | — | — | — | 0.8% | — | — |
| Xanthan gum | 0.2% | — | 0.2% | 1.5% | 0.5% | — | 1.8% | 0.2% | 1.1% | 0.9% |
| Hydroxyethyl ethylcellulose | 0.1% | — | — | 0.1% | — | 0.1% | 0.1% | — | — | — |
| Benzophenone-4 | — | 0.1% | 0.2% | — | — | — | — | 0.2% | — | 0.1% |
| Menthol | 0.1% | — | 0.1% | — | — | 0.1% | — | 0.1% | 0.1% | 0.1% |
| Caffeine | — | — | 0.1% | — | 0.1% | — | — | 0.1% | — | 0.1% |
| Benzyl alcohol | 0.1% | — | — | — | — | 0.1% | — | 0.1% | — | — |
| Coumarin | 0.1% | — | 0.1% | 0.1% | — | — | 0.1% | 0.1% | — | 0.1% |
| Hydrolysed wheat protein | — | — | 0.1% | 0.1% | 0.1% | 0.2% | 0.2% | 0.1% | — | — |
| Panthenol | 0.1% | 0.1% | — | 0.1% | 0.1% | 0.1% | 0.1% | — | 0.1% | 0.1% |
| Citric acid | | | | | to pH 5.2 | | | | | |
| Perfumes, Dyes, Preservatives | | | | | q.s. | | | | | |

TABLE 41

Further formulation examples

| | 41a | 41b | 41c | 41d | 41e | 41f | 41g | 41h | 41i | 41j |
|---|---|---|---|---|---|---|---|---|---|---|
| Water | | | | | to 100% | | | | | |
| Product example E | 3.5% | 3.0% | 2.5% | 4.0% | 3.0% | 4.0% | 6.0% | 4.0% | 5.0% | 4.0% |
| MIPA-Laureth sulphate | 10.5% | 5.0% | — | — | — | — | — | — | — | — |
| Sodium C14-16 olefin sulphonate | — | — | 8.0% | — | — | — | — | — | 3.5% | — |
| Coco betaine | — | 4.0% | — | 5.5% | — | — | 4.0% | — | 3.5% | — |
| Cocamidopropyl betaine | 2.0% | — | 4.0% | — | 5.0% | 5.0% | — | — | — | 4.0% |
| Sodium cocoamphopropionate | — | — | 1.0% | — | 2.0% | — | 1.5% | 4.0% | 2.0% | 3.5% |
| Coco glucoside | — | 2.5% | — | 2.5% | 3.0% | — | 4.5% | 3.5% | 2.0% | 0.5% |
| Sodium cocoyl glutamate | — | — | — | 1.5% | 1.0% | 1.5% | 1.5% | 1.5% | 0.8% | 0.3% |
| Laurie acid | — | 0.5% | — | — | — | 1.0% | — | 2.0% | — | 4.5% |
| Sodium cocoyl glycinate | — | — | — | 2.5% | — | 5.0% | — | — | 0.8% | 0.5% |
| Sodium cocoyl sarcosinate | — | 0.7% | 0.5% | — | — | 1.0% | 0.5% | — | — | — |
| Dicaprylylether | 0.5% | — | — | — | — | 0.2% | — | — | — | — |
| Glycerol | 0.5% | 0.3% | 0.5% | 1.5% | 0.4% | 0.5% | 1.0% | 0.5% | 0.3% | 1.0% |
| Polysorbate 20 | 0.5% | — | — | — | — | 0.5% | — | — | — | 0.4% |
| Polyglyceryl-4 laurate | 0.5% | — | 0.4% | 0.3% | — | — | 0.5% | — | 1.1% | — |
| Polyquaternium-37 | 0.4% | — | — | 0.1% | — | — | — | 0.2% | 0.1% | — |

TABLE 41-continued

Further formulation examples

| | 41a | 41b | 41c | 41d | 41e | 41f | 41g | 41h | 41i | 41j |
|---|---|---|---|---|---|---|---|---|---|---|
| Hydroxypropyl guar hydroxypropyltrimonium chloride | — | 0.2% | 0.1% | 0.2% | — | — | 0.3% | — | 0.2% | — |
| Cassia hydroxypropyltrimonium chloride | — | 0.1% | — | — | 0.2% | — | — | — | — | — |
| Sodium hydroxypropyl starch phosphate | 0.2% | — | — | — | — | 0.4% | — | — | — | 0.5% |
| Hydroxypropyl methylcellulose | 0.2% | — | — | 0.2% | 0.2% | — | — | — | 0.2% | — |
| Dimethicone | 0.2% | — | — | — | — | 1.0% | — | — | 0.3% | — |
| Aminopropyl dimethicone | 0.2% | 0.4% | — | — | — | 0.5% | — | — | — | 0.5% |
| Palmitamidopropyltrimonium chloride | 0.3% | — | 0.5% | — | — | — | — | — | 0.4% | — |
| *Persea gratissima* (avocado) oil | 0.1% | 1.1% | — | 0.1% | 0.2% | — | 0.3% | — | 0.1% | 0.1% |
| *Butyrospermum parkii* butter extract | 0.2% | — | 0.1% | — | — | 0.3% | — | — | — | — |
| *Prunus amygdalus dulcis* oil | 0.2% | — | 0.2% | 0.2% | — | — | 0.2% | 0.5% | — | — |
| Glycol distearate | 0.5% | 0.7% | — | — | 0.5% | 0.8% | — | — | 0.4% | 0.3% |
| Carbomer | — | 0.3% | — | — | — | 0.5% | 0.7% | — | 0.5% | — |
| Sodium hydroxide, 25% | — | 0.5% | — | — | — | 0.7% | 1.0% | — | 0.8% | — |
| Isostearamide MIPA; Glyceryl laurate | 0.7% | — | 0.8% | — | 0.3% | 0.3% | — | 0.4% | — | 0.3% |
| Sorbitan sesquicaprylate | — | — | 0.2% | 1.0% | — | — | 0.4% | 1.0% | — | 0.7% |
| Sodium chloride | 0.8% | — | 0.3% | 0.2% | 0.5% | — | — | 2.0% | — | — |
| PEG-18 Glyceryl oleate/cocoate | 0.8% | — | — | — | — | 0.6% | — | — | — | 0.9% |
| Xanthan gum | — | 1.0% | 0.2% | 1.0% | — | 0.2% | 0.3% | — | — | 0.2% |
| Algin | — | 0.2% | — | — | 1.0% | — | — | — | 1.2% | — |
| Caragenaan | 0.5% | — | — | 0.3% | — | — | — | 0.3% | — | 0.2% |
| Silica | 0.1% | — | 0.1% | — | — | 0.2% | — | — | 0.2% | 0.1% |
| Cetearyl alcohol | 0.2% | — | — | — | 0.3% | 0.2% | — | — | — | 0.3% |
| Benzophenone-4 | 0.1% | 0.1% | 0.2% | — | 0.2% | 0.2% | — | — | — | 0.1% |
| Tetrasodium EDTA | 0.1% | 0.1% | — | 0.1% | 0.1% | 0.2% | 0.1% | — | 0.2% | 0.1% |
| Octopirox | 0.2% | — | — | — | — | 0.1% | — | — | — | — |
| Zinc PCA | — | — | 0.1% | — | — | — | — | — | — | 0.1% |
| Creatine | 0.1% | — | 0.1% | 0.1% | — | 0.1% | 0.1% | 0.1% | — | 0.1% |
| Hydrolysed collagen | — | — | — | 0.1% | — | 0.1% | — | 0.1% | 0.1% | 0.1% |
| Salicylic acid | 0.1% | — | — | — | 0.1% | 0.1% | — | — | 0.1% | 0.1% |
| Panthenol | 0.1% | 0.1% | — | 0.1% | 0.1% | 0.1% | 0.1% | — | 0.1% | 0.1% |
| Lactic acid | 0.2% | — | 0.2% | — | 0.1% | 0.5% | 0.3% | — | 0.2% | — |
| PEG-14M | 0.3% | — | — | — | — | 0.4% | — | — | — | 0.3% |
| 1,2-Hexanediol | 0.3% | — | — | — | — | 0.3% | — | 0.2% | — | — |
| Citric acid | to pH 5.5 | | | | | | | | | |
| Perfumes, Dyes, Preservatives | q.s. | | | | | | | | | |

TABLE 42

List of raw materials used

| INCI | Trade name, company |
|---|---|
| 1,2-Hexanediol | Hydrolite-6 841129, Symrise |
| Acrylates/beheneth-25 methacrylate copolymer | Novethix L-10 Polymer, Lubrizol |
| Acrylates/C10-30 alkyl acrylate crosspolymer | TEGO Carbomer 841 SER, Evonik Industries AG, 100% |
| Algin | Hydagen 558 P, BASF |
| Allantoin | Allantoin, DSM Nutritional Products, Inc. |
| *Aloe barbadensis* leaf juice | Aloe-Con UP 40, Florida Food Products Inc. |
| alpha-Isomethyl ionone | alpha-Isomethylionone, Chemos GmbH |
| Alumina | Aeroxide Alu C, Evonik Industries AG |
| Aluminium chlorohydrate | Locron L, Clariant |
| Ammonium lauryl sulphate | Empicol AL 70, Albright & Wilson UK Limited |
| Aminopropyl dimethicone | ABIL ® Soft AF 200, Evonik Industries |
| Amodimethicone | DC 949, Dow Corning, 100% |
| *Argania spinosa* oil (*Argania spinosa* kernel oil) | Argan Oil, DSM Nutritional Products Ltd. |
| Benzophenone-4 | Uvinul MS 40, BASF Corporation |
| Benzoic acid | OriStar HSB, Orient Stars LLC |
| Benzyl alcohol | Microcare BNA, THOR PERSONAL CARE SAS |
| Benzyl salicylate | Seridefrizz Intense, Cheemyunion Quimica Ltda. |
| Butylene glycol | Butylene Glycol, Oxea Corporation |
| *Butyrospermum parkii* butter extract | Cosmosil 600, International Cosmetic Science Centre |
| Caffeine | Caffeine, Merck KGaA/EMD Chemicals, Inc. |
| *Camellia oleifera* seed oil | Camellia Sasanqua Oil, Ikeda Corporation |
| Caprylyl glycol | Sensiva SC 10, Schülke& Mayr GmbH |
| Capryl/capramidopropyl betaine | TEGO Betain 810, Evonik Industries AG, 38% |
| Caprylic/capric triglyceride | TEGOSOFT CT, Evonik Industries AG, 100% |
| Carrageenan | Genugel Carrageenan, CP Kelco |
| Carbomer | TEGO Carbomer 140, Evonik Industries AG, 100% |
| Cassia hydroxypropyltrimonium chloride | Formularbeginn Sensomer ST 250-Polymer, Lubrizol Formularende |
| Cellulose | Arbocel A300, J. Rettenmaier & Söhne |

TABLE 42-continued

List of raw materials used

| INCI | Trade name, company |
|---|---|
| Cetearyl Alcohol | TEGO Alkanol 1618, Evonik Industries AG, 100% |
| Cetyl ricinoleate | TEGOSOFT CR, Evonik Industries AG, 100% |
| Cetrimonium bromide | Rhodaquat M-242B/99, Rhodia |
| *Chamomilla recutita* (*matricaria*) extract | Recentia CR, AkzoNobel Global Personal Care |
| Citral | Citral FF, Symrise AG |
| Citric acid | Citric Acid USP Granular, DSM Nutritional Products, Inc. |
| *Citrus aurantifolia* (lime) oil | AEC Lime Oil, A & E Connock, Perfumery & Cosmetics Ltd. |
| *Cistus incanus* extract; Maltodextrin | TEGO Pearl N 300, Evonik Industries AG |
| Cocamide DEA | REWOMID DC 212 S, Evonik Industries AG, 100% |
| Cocamide MEA | REWOMID D 212, Evonik Industries AG, 100% |
| Cocamidopropyl betaine | TEGO Betain F 50, Evonik Industries AG, 38% |
| Coco glucoside | Plantacare 818 UP, BASF Cognis, 51% |
| Coco betaine | Dehyton AB 30, BASF Cognis, 31% |
| Coumarin | Rhodiascent extra pure, Rhodia Organics |
| Creatine | TEGO Cosmo C 100, Evonik Industries AG, 100% |
| Decyl glucoside | Plantacare 2000 UP, BASF Cognis |
| Dicaprylylether | Cetiol OE, BASF Cognis |
| Dehydroacetic acid | Unisept DHA (Universal Preserv-A-Chem, Inc.) |
| Dimethicone | DC 200 Fluid 100 cSt, Dow Corning, 100% |
| Disodium cocoamphodiacetate | REWOTERIC ® AM 2 C NM, Evonik Industries, 39%-ig |
| Disodium cocoyl glutamate | Planatpon ACG LC, BASF Cognis |
| Disodium EDTA | Dissolvine NA-2-P, AkzoNobel Global Personal Care |
| Disodium lauryl sulphosuccinate | REWOPOL SB F 12 P, Evonik Industries AG, 95% |
| Ethylhexyl stearate; Phenoxyethanol; Polyglyceryl-4 laurate; Sorbitan laurate; Dilauryl citrate | TEGO ® Wipe Flex (Evonik Industries AG) |
| Geraniol | Nerol 800, International Flavors & Fragrances Inc. |
| Glucose | Organic Biovert Substrate, Lonza |
| Glycerol | Glycerol EP, vegetable, Spiga Nord, 99.7% |
| Glyceryl caprylate | Dermosoft GMCY, Dr. Straetmans |
| Glyceryl glucoside | Hydagen GG, BASF Cognis |
| Glyceryl oleate | TEGIN O V, Evonik Industries AG, 100% |
| *Glycine soya* (soybean) oil | Cropure Soybean, Croda Europe, Ltd. |
| Glycol distearate | TEGIN G 1100, Evonik Industries AG, 100% |
| Guar hydroxypropyltrimonium chloride | Cosmedia Guar C 261, BASF Personal Care and Nutrition Gmbh/Jaguar C-17, Rhodia Inc. and andere |
| *Helianthus annuus* (sunflower) seed oil | AEC Sunflower Oil, A & E Connock, Perfumery & Cosmetics Ltd. |
| Hydrogenated castor oil | Cutina HR Powder, BASF Personal Care and Nutrition Gmbh |
| Hydrolysed collagen | Nutrilan H, BASF Personal Care and Nutrition Gmbh |
| Hydrolysed keratin | Kerasol, Croda, Inc. |
| Hydrolysed wheat protein | Gluadin WLM, BASF Cognis |
| Hydrolysed wheat starch | Cropeptide W, Croda, Inc. |
| Hydroxyethyl ethylcellulose | Structure Cel 4400 E, AkzoNobel Global Personal Care |
| Hydroxypropyl guar hydroxypropyltrimonium chloride | Jaguar C-162, Rhodia, 100% |
| Hydroxypropyl methylcellulose | TEGOCEL HPM 50, Evonik Industries AG, 100% |
| Isopropyl myristate | TEGOSOFT M, Evonik Industries AG, 100% |
| Isostearamide MIPA; Glyceryl laurate | ANTIL SPA 80, Evonik Industries AG, 100% |
| Lactic acid | AEC Lactic Acid, A & E Connock, Perfumery & Cosmetics Ltd. |
| Lactis proteinum | AEC Whey Protein, A & E Connock, Perfumery & Cosmetics Ltd. |
| Laureth-4 | TEGO Alkanol L 4, Evonik Industries AG, 100% |
| Laureth-5 carboxylic acid | Marlowet 1072, Sasol Germany GmbH-Marl |
| Lauric acid | Prifrac 2920, Croda Europe, Ltd. |
| Lauryl glucoside | Plantacare 1200 UP, BASF Cognis, 50% |
| Lecithin | AEC Lecithin Powder, A & E Connock, Perfumery & Cosmetics Ltd. |
| Limonene | Dipentene No. 122, Hercules Inc. |
| Linalool | Lipofresh, Lipo Chemicals, Inc. |
| Magnesium chloride | OriStar MCL, Orient Stars LLC |
| Maltodextrin | Farmal MD 10, Corn Products International |
| *Malva sylvestris* leaf extract | Herbasec Mallow Leaves, Cosmetochem International AG |
| *Mangifera indica* (mango) fruit extract | Mango Extract, Draco Natural Products |
| Menthol | OriStar HSB, Orient Stars LLC |
| MIPA-Laureth sulphate | Zetesol 2056, Zschimmer & Schwarz GmbH |
| Octopirox | Octopirox, Clariant Intl. Ltd. |
| *Olea europaea* (olive) fruit oil | Cropure Olive, Croda Europe, Ltd. |
| Palmitamidopropyltrimonium chloride) | VARISOFT PATC, Evonik Industries AG, 60% |
| Panthenol | D-Panthenol USP, BASF, 100% |
| PEG-120 Methyl glucose dioleate | ANTIL 120 Plus, Evonik Industries AG, 100% |
| PEG-14M | Polyox WSR-205, The Dow Chemical Company |
| PEG-18 Castor oil dioleate | Marlowet CG, Sasol Germany GmbH |
| PEG-18 Glyceryl oleate/cocoate | ANTIL 171 Plus, Evonik Industries AG, 100% |
| PEG-200 Hydrogenated glyceryl palmate; PEG-7 Glyceryl cocoate | REWODERM LI S 80, Evonik Industries AG, 100% |
| PEG-3 Distearate | TEGIN D 1102, Evonik Industries AG, 100%; Cutina TS, BASF Cognis, 100% |
| PEG-40 Hydrogenated castor oil | TAGAT L 40, Evonik Industries AG, 100% |
| PEG-40 Sorbitan peroleate | Arlatone T, Croda |
| PEG-6 Caprylic/capric glycerides | TEGOSOFT DEC, Evonik Industries AG, 100% |
| PEG-7 Glyceryl cocoate | TEGOSOFT GC, Evonik Industries AG, 100% |
| *Persea gratissima* (avocado) oil | Cropure Avocado, Croda Europe, Ltd. |
| Petrolatum | Merkur 115, Sasol Wax GmbH |
| Phenethyl alcohol | Etaphen, Vevy Europe SpA |
| Phenoxyethanol | S&M Phenoxyethanol, Schülke & Mayr GmbH |
| Phenoxyethanol; Ethylhexyl glycerol | Euxyl PE 9010, Schülke & Mayr GmbH |
| Phenoxyethanol; Methylparaben; Ethylparaben; Butylparaben; Propylparaben; Isobutylparaben | Euxyl K 300, Schuelke & Mayr GmbH |
| Polyaminopropyl biguanide | Microcare MBG, Thor |
| Polyglyceryl-3 palmitate | Dermofeel PP, Dr. Straetmans |
| Polyglyceryl-4 caprate | TEGOSOFT PC- 41, Evonik Industries AG, 100% |
| Polyglyceryl-6 caprylate; Polyglyceryl-4 caprate; Propylene glycol | TEGO Betain 55, Evonik Industries AG 35% |
| Polyquatemium-10) | Polymer JR 400, Amerchol, 100% |
| Polyquatemium-11 | Dehyquart CC 11, BASF Personal Care and Nutrition Gmbh/Luviquat PQ 11 PN, BASF Corporation |
| Polyquaternium-37 | Cosmedia Ultragel 300, BASF Personal Care and Nutrition Gmbh |

TABLE 42-continued

List of raw materials used

| INCI | Trade name, company |
|---|---|
| Polyquaternium-7 | Merquat 550, Nalco, 100% |
| Polysorbate 20 | TEGO SML 20, Evonik Industries AG, 100% |
| Potassium sorbate | Euxyl K 712, Schülke & Mayr GmbH |
| Propylene glycol | Euxyl K 320, Schülke & Mayr GmbH |
| Propylene glycol; PEG-55 Propylene glycol oleate | ANTIL 141 Plus, Evonik Industries AG, 100% |
| *Prunus amygdalus dulcis* (sweet almond) oil | Cropure Almond, Croda Europe, Ltd. |
| *Prunus cerasus* (bitter cherry) fruit extract | *Prunus Cerasus* Fruit, Kirschen Extract, Botanica GmbH |
| *Ricinus communis* seed oil | Lipovol CO, Lipo Chemicals |
| Salicylic acid | OriStar HSB, Orient Stars LLC |
| Silica | Aerosil 130, Evonik Degussa GmbH |
| Silicone quaternium-22 | ABIL T Quat 60, Evonik Industries AG, 65% |
| Silicone quaternium-22; Polyglycerol-3 caprate; Dipropylene glycol; Cocamidopropyl betaine | ABIL B 45, Evonik Industries AG, 30% |
| *Simmondsia chinensis* (jojoba) seed oil | AEC Jojoba Oil Refined, A & E Connock, Perfumery & Cosmetics Ltd. |
| Sodium benzoate | Euxyl K 712, Schülke & Mayr GmbH |
| Sodium C14-16 olefin sulphonate | Bioterge AS-40 AOS, Stepan |
| Sodium cetearyl sulphate | Lanette E, BASF Personal Care and Nutrition Gmbh |
| Sodium cocoamphoacetate | REWOTERIC AM C, Evonik Industries AG, 32% |
| Sodium cocoamphopropionate | REWOTERIC AM KSF 40, Evonik Industries AG, 40% |
| Sodium coco sulphate | Texapon HC G, BASF Cognis |
| Sodium cocoyl glutamate | Plantapon ACG HC, BASF Cognis |
| Sodium cocoyl glycinate | Hostapon SG, Clariant; Amilite GCS-11, Ajinomoto |
| Sodium cocoyl sarcosinate | Crodasinic MS, Croda |
| Sodium/disodium cocoyl glutamate | PERLASTAN ® SC 25 NKW, Schill&Seilacher, 25%, |
| Sodium hydroxide | Unichem SOHYD, Universal Preserv-A-Chem, Inc. |
| Sodium hydroxypropyl starch phosphate | Pure-Gel, Grain Processing Corporation |
| Sodium isethionate | Hostapon SI, Company Clariant International Ltd |
| Sodium lactate | Sodium Lactate Solution About 50%, Merck KGaA/EMD Chemicals, Inc. |
| Sodium lactate; Sodium PCA; Glycine; Fructose; Urea; Niacinamide; Inositol; Sodium benzoate; Lactic acid | LACTIL, Evonik Industries AG, 100% |
| Sodium laureth sulphate | Texapon NSO, BASF Cognis, 28% |
| Sodium lauroamphoacetate | ColaTeric SLAA, Colonial Chemical Inc |
| Sodium lauroyl isethionate | Yongan SLI , Huanggang Yongan Pharmaceutical Co., Ltd |
| Sodium lauroyl methyl isethionate | Iselux, Innospec Active Chemicals |
| Sodium lauryl sulphate | Texapon LS 35, BASF Cognis, 30% |
| Sodium trideceth sulphate | Rhodapex EST-30, Rhodia |
| Sorbitan caprylate | Sorbon S-10, Toho Chemical Industry Co., Ltd. |
| Sorbitan sesquicaprylate) | ANTIL Soft SC, Evonik Industries AG, 100% |
| Stearic acid | Pristerene 4922, Croda Europe, Ltd. |
| Styrene/acrylates copolymer | Neolone PE, The Dow Chemical Company |
| Sucrose cocoate | TEGOSOFT LSE 65 K, Evonik Industries AG, 100% |
| Tetrasodium EDTA | Neolone PE, The Dow Chemical Company |
| Tocopherol | Euxyl K 700, Schülke & Mayr GmbH |
| Trideceth-9 | Marlipal O 13/90, Sasol Germany GmbH - Marl |
| *Triticum vulgare* germ oil | Cropure Wheatgerm, Croda Europe, Ltd. |
| Xanthan gum | Keltrol CG-SFT, CP Kelco, 100% |
| *Zea mays* (corn) germ oil | AEC Corn Germ Oil, A & E Connock, Perfumery & Cosmetics Ltd. |

TABLE 42-continued

List of raw materials used

| INCI | Trade name, company |
|---|---|
| Zinc PCA | Zincidone, UCIB, Solabia Group |
| Zinc pyrithione | Microcare ZP, THOR PERSONAL CARE SAS |

While the present invention has been particularly shown and described with respect to various embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A polyglycerol partial ester of general formula I

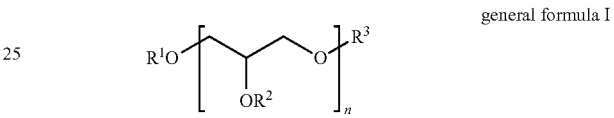

general formula I where
n=2 to 16,
$R^1$, $R^2$, $R^3$=are, independently of one another, identical or different, selected from H, $R^4$ and $R^5$, where
$R^4$=saturated or unsaturated acyl residue having 6-22 carbon atoms and comprising no hydroxyl groups,
$R^5$=saturated or unsaturated acyl residue having 6-22 carbon atoms and comprising at least one hydroxyl group or an acyl residue of an oligomer of saturated or unsaturated acyl residues having 6-22 carbon atoms and comprising at least one hydroxyl group,
wherein the acyl residues $R^4$ to $R^5$ are present in a molar ratio in a range of 95:5 to 5:95.

2. The polyglycerol partial ester according to claim 1, wherein $R^4$ and $R^5$ are acyl residues of fatty acids.

3. The polyglycerol partial ester according to claim 1, wherein at least 50 mol % of the $R^4$ acyl residues are selected from capryloyl, caproyl and lauroyl residues, based on all $R^4$ residues in the polyglycerol partial ester.

4. The polyglycerol partial ester according to claim 1, wherein $R^5$ is selected from ricinoyl and hydroxystearoyl residues, their oligomers and mixtures thereof.

5. The polyglycerol partial ester according to claim 1, wherein at least 90 mol % of the $R^5$ acyl residues comprise ricinoyl residues or a mixture of ricinoyl and hydroxystearoyl residues, based on all $R^5$ residues in the polyglycerol partial ester.

6. The polyglycerol partial ester according to claim 1, wherein $R^5$ is selected from ricinoyl residues.

7. The polyglycerol partial ester according to claim 1, wherein a weight ratio of the polyglyceryl residue to the sum total of the acyl residues $R^4$ and $R^5$ is 85:15 to 55:45.

8. A method for preparing polyglycerol partial esters comprising the steps of:
A) providing a polyglycerol having a mean degree of polymerisation n=2 to 16,
B) acylating some of the hydroxyl groups of the polyglycerol with at least one first carboxylic acid derivative of one or more first, saturated or unsaturated carboxylic acids having 6-22 carbon atoms and comprising no hydroxyl groups, and at least one second carboxylic acid derivative of one or more second, saturated or unsaturated carboxylic acids having 6-22 carbon atoms and comprising at least one hydroxyl group or an oligomer of the second carboxylic acid, said carboxylic acid derivatives are selected from carboxylic acids and carboxylic esters, and wherein a molar ratio of the acyl residues of the first carboxylic acid derivative to those of the second carboxylic acid derivative is in a range of 95:5 to 5:95.

9. The method according to claim 8, wherein during said acylating
at least one first carboxylic acid and at least one second carboxylic acid,
at least one first carboxylic ester and at least one second carboxylic acid,
at least one first carboxylic acid and at least one second carboxylic ester,
at least one first carboxylic ester and at least one second carboxylic ester,
at least one first carboxylic acid and at least one first carboxylic ester and at least one second carboxylic acid,
at least one first carboxylic acid and at least one first carboxylic ester and at least one second carboxylic ester,
at least one first carboxylic acid and at least one second carboxylic acid and at least one second carboxylic ester,
at least one first carboxylic ester and at least one second carboxylic acid and at least one second carboxylic ester,
or
at least one first carboxylic acid and at least one first carboxylic ester and at least one second carboxylic acid and at least one second carboxylic ester,
are used.

10. The method according to claim 8, wherein at least 50 mol % of the first carboxylic acids are selected from caprylic acid, capric acid and lauric acid, based on the acyl residues of all the first carboxylic acid derivatives.

11. The method according to claim 8, wherein at least 90 mol % of the second carboxylic acids are selected from ricinoleic acid and hydroxystearic acid, based on the acyl residues of all the second carboxylic acid derivatives.

12. The method according to claim 8, wherein at least 90 mol % of the second carboxylic acids comprise ricinoleic acid and hydroxystearic acid, and the second carboxylic acids have a molar ratio of ricinoleic acid residues to hydroxystearic acid residues in a range of 100 to 0.1 to 50 to 50, based on the acyl residues of all the second carboxylic acid derivatives.

13. The method according to claim 8, wherein a weight ratio of the polyglycerol to the sum total of the acyl residues of the first and second carboxylic acid derivatives used is 85:15 to 55:45.

14. The method according to claim 8, wherein a molar ratio of the acyl residues of saturated to unsaturated carboxylic acid derivatives used in said acylating is 99:1-1:99.

15. A polyglycerol partial ester obtained by a method according to claim 8.

16. A formulation comprising at least one polyglycerol partial ester according to claim 1.

17. The formulation according to claim 16, comprising:
0.1% by weight to 40% by weight of said polyglycerol partial ester,
0.01% by weight to 40% by weight of oil-soluble substance, and
10% by weight to 98% by weight of water.

18. A method comprising:
mixing at least one polyglycerol partial ester according to at claim 1 with at least one oil-soluble substance to provide a mixture; and
treating said mixture with water, wherein said at least one polyglycerol partial ester solubilizes said least one oil-soluble substance upon said treating with water.

* * * * *